United States Patent
Gruenanger et al.

(10) Patent No.: US 9,428,443 B2
(45) Date of Patent: Aug. 30, 2016

(54) METHOD FOR PRODUCING AMINO ACIDS

(71) Applicant: BASF SE, Ludwigshafen (DE)

(72) Inventors: Christian Gruenanger, Mannheim (DE); Roland Bou Chedid, Mannheim (DE); Markus Christian Biel, Mannheim (DE); Johann-Peter Melder, Boehl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/893,661

(22) PCT Filed: May 14, 2014

(86) PCT No.: PCT/EP2014/059867
§ 371 (c)(1),
(2) Date: Nov. 24, 2015

(87) PCT Pub. No.: WO2014/187712
PCT Pub. Date: Nov. 27, 2014

(65) Prior Publication Data
US 2016/0122288 A1    May 5, 2016

(30) Foreign Application Priority Data
May 24, 2013   (EP) .................................... 13169152

(51) Int. Cl.
*C07C 227/00* (2006.01)
*C07C 227/08* (2006.01)

(52) U.S. Cl.
CPC .................. *C07C 227/08* (2013.01)

(58) Field of Classification Search
CPC .................................. C07C 227/08

USPC ......................................................... 562/575
See application file for complete search history.

(56) References Cited

U.S. PATENT DOCUMENTS

| | | |
|---|---|---|
| 2004/0092725 A1 | 5/2004 | Hatakeda et al. |
| 2013/0012737 A1 | 1/2013 | Tani et al. |
| 2013/0158294 A1 | 6/2013 | Bou Chedid et al. |

OTHER PUBLICATIONS

European Search Report issued Oct. 25, 2013 in Patent Application No. 13169152 (with English translation of categories of cited documents).
International Search Report issued Jun. 23, 2014 in PCT/EP2014/059867 (with English language translation).
Sadaichi Nakamura, et al., "Studies on the Formation of Amino Acids from Keto acids" Journal of the Agricultural Chemical Society of Japan, vol. 24, No. 4, XP008165506, Jan. 1, 1950, pp. 185-187 (with English language translation).
J. C. Watkins, "The Synthesis of Some Acidic Amino Acids Possessing Neuropharmacological Activity" Journal of Medicinal and Pharmaceutical Chemistry, vol. 5, XP001156267, Nov. 1962, pp. 1187-1199.

*Primary Examiner* — Sikarl Witherspoon
(74) *Attorney, Agent, or Firm* — Oblon, McClelland, Maier & Neustadt, L.L.P.

(57) ABSTRACT

Process for the preparation of alkali metal salts of glycine or of racemic α-amino acids of the general formula (I)

$$R^1\text{—CH(NH}_2\text{)—COOH} \qquad (I)$$

in which $R^1$ is selected from hydrogen, $CH_3$, $C_2H_5$, $CH(CH_3)_2$, $(CH_2)_2COOH$ and $CH_2OH$, wherein an alkali metal salt of the corresponding α-ketocarboxylic acid or glyoxalic acid is reacted in the presence of at least one heterogeneous catalyst, which comprises at least one transition metal, in the presence of hydrogen with at least one nitrogen compound at temperatures in the range from 50 to 200° C., where the nitrogen compound is selected from primary and secondary amines and ammonia.

10 Claims, No Drawings

METHOD FOR PRODUCING AMINO ACIDS

The present invention relates to a process for the preparation of alkali metal salts of glycine or of racemic α-amino acids of the general formula (I)

$$R^1\text{---}CH(NH_2)\text{---}COOH \quad (I)$$

in which $R^1$ is selected from hydrogen, $CH_3$, $C_2H_5$, $CH(CH_3)_2$, $(CH_2)_2COOH$ and $CH_2OH$,
wherein an alkali metal salt of the corresponding α-ketocarboxylic acid or glyoxalic acid is reacted in the presence of at least one heterogeneous catalyst, which comprises at least one transition metal, in the presence of hydrogen with at least one nitrogen compound at temperatures in the range from 50 to 200° C., where the nitrogen compound is selected from primary and secondary amines and ammonia.

Amino acids have numerous fields of application. For example, L-amino acids are used for peptide synthesis and for protein synthesis. Though racemic amino acids are also valued intermediates.

The preparation of racemic amino acids by the Strecker synthesis is known per se. It is disadvantageous that with hydrocyanic acid and/or the corresponding cyanides, very toxic substances are required, which facilitate the need for special safety precautions.

U.S. 2004/092725 discloses a process for synthesizing α-amino acids from corresponding α-hydroxycarboxylic acids by reaction with ammonia at high pressure and preferably at least 300° C. However, the yields are low. For example, the synthesis of glycine at 374° C. with a yield of 4.3% and the synthesis of α-alanine at 374° C. with a yield of 2.8% is disclosed. However, yields of this type are unsatisfactory in industrial processes. Moreover, the products obtained are mostly dark in color and then require a complex purification process.

U.S. 2013/0012737 discloses a process for the preparation of the sodium salt of 2-amino-4-methylthiobutyric acid, in which salts of the corresponding keto acids are subjected to reductive amination.

However, other α-keto acids decompose very easily, especially at elevated temperatures and therefore do not appear to be suitable as a precursor for preparing racemic amino acids.

The object was thus to provide a process by means of which racemic α-amino acids can be obtained in good yields.

Accordingly, the process defined at the start has been found, within the context of the present invention also called process according to the invention.

In the case of the preparation of glycine, which is achiral, no racemate is obtained, but glycine.

Within the context of the present invention, glyoxalic acid is also considered to be an α-ketocarboxylic acid of the general formula (II) where $R^1$=H.

To carry out the process according to the invention, the starting point is at least one corresponding α-ketocarboxylic acid, i.e. an α-ketocarboxylic acid of the general formula (II), $$R^1\text{---}C(=O)\text{---}COOH \quad (II)$$

in which $R^1$ is selected from hydrogen, $CH_3$, $C_2H_5$, $CH(CH_3)_2$, $(CH_2)_2COOH$ and $CH_2OH$, preferably $R^1$ is $CH_3$;
for example a mixture of two or three α-ketocarboxylic acids of the general formula (II). Preference is given to using precisely one α-ketocarboxylic acid of the general formula (II).

Preferred examples of α-ketocarboxylic acids of the general formula (II) are glyoxalic acid, 2-oxoglutaric acid, 3-hydroxy-2-oxopropionoic acid, 2-oxo-4-methylbutyric acid and in particular pyruvic acid.

α-Ketocarboxylic acid of the general formula (II) is used in partially or completely neutralized form, preferably in completely neutralized form, and specifically as alkali metal salt such as, for example, as potassium salt and preferably as sodium salts. Very particularly preferably, α-ketocarboxylic acid of the general formula (II) is used with an excess of base, where base can be selected from alkali metal (hydrogen)carbonate and alkali metal hydroxide, for example sodium hydrogen carbonate, potassium hydrogen carbonate, sodium carbonate, potassium carbonate, potassium hydroxide and in particular sodium hydroxide.

In one embodiment of the present invention, the process according to the invention is carried out in an aqueous medium. This is to be understood as meaning that alkali metal salt of α-ketocarboxylic acid of the general formula (II) is dissolved in water or in a mixture which comprises to at least 75% by volume water and can comprise in total up to 25% by volume organic solvent, for example tetrahydrofuran or N,N-dimethylformamide, where % by volume is based on the total continuous phase. Preferably, no organic solvent or only 0.1 to 5% by volume organic solvent is used, based on the continuous phase. In another variant, α-ketocarboxylic acid of the general formula (II) can be dissolved or suspended in water or in a mixture which comprises to at least 75% by volume water and in total up to 25% by volume organic solvent, for example tetrahydrofuran or N,N-dimethylformamide, and then neutralized at least partially and preferably completely with a preferably aqueous solution of alkali metal (hydrogen) carbonate and alkali metal hydroxide.

In one embodiment of the present invention, the process according to the invention is carried out at a pH in the range from 6 to 14, particularly preferably 7 to 13.5.

According to the invention, alkali metal salt of α-ketocarboxylic acid of the general formula (II) is reacted with at least one nitrogen compound, where nitrogen compound is selected from primary amines, preferably secondary amines and even more preferably ammonia. Examples of primary amines are in particular $C_1$-$C_{10}$-alkylamines, for example methylamine, ethylamine, isopropylamine, tert-butylamine, n-decylamine, also aromatic amines such as aniline, $C_3$-$C_7$-cycloalkylamines such as, for example, cyclohexylamine and monoethanolamine. Examples of secondary amines are di-$C_1$-$C_{10}$-alkylamines, in particular dimethylamine, diethylamine and diisopropylamine, also di-$C_2$-$C_4$-hydroxyalkyleneamines, in particular diethanolamine, also mono-$C_1$-$C_{10}$-alkylmono-$C_2$-$C_4$-hydroxyalkyleneamines, for example N-methyl-N-ethanolamine, also cyclic secondary amines such as piperidine and morpholine. Further suitable nitrogen compounds are iminodicarboxylic acids, in particular iminodiacetic acid.

In a preferred embodiment of the present invention, the nitrogen compound selected is ammonia, i.e. the reaction is with ammonia. Ammonia can be added to the reaction mixture in the form of liquid ammonia, gaseous ammonia or ammoniacal water ("$NH_4OH$"). If it is desired to add ammonia in the form of an ammonium salt, then it is preferred to add ammonia in combination with at least one strong base, for example in combination with NaOH or KOH. It is preferred to add ammonia in the form of liquid ammonia or ammoniacal water.

In one embodiment, α-ketocarboxylic acid of the general formula (II) and nitrogen compound are used in a molar ratio in the range from 1:1 to 1:100, preferably in the range from 1:2 to 1:50, particularly preferably in the range from 1:3 to 1:30. Here, the fraction of nitrogen compound refers to the sum of all nitrogen compounds used as reactants.

In one embodiment, α-ketocarboxylic acid of the general formula (II) and ammonia are used in a molar ratio in the range from 1:1 to 1:100, preferably in the range from 1:2 to 1:50, particularly preferably in the range from 1:3 to 1:30.

The process according to the invention is carried out in the presence of hydrogen, i.e. $H_2$. In one embodiment of the present invention, the process according to the invention is carried out such that in total a molar ratio of α-ketocarboxylic acid of the general formula (II) to hydrogen in the range from 1:1 to 1:90, preferably 1:2 to 1:30, is established.

In one embodiment of the present invention, hydrogen can be diluted by means of a gas that is inert under the reaction conditions of the process according to the invention, for example with nitrogen or with at least one noble gas, for example with argon.

The process according to the invention is carried out in the presence of at least one heterogeneous catalyst which comprises at least one transition metal. The heterogeneous catalysts here may be:
  (i) metal-containing catalysts supported on a solid support which is present in particulate form,
  (ii) metal-containing catalysts supported on a solid support which is in nonparticulate form,
  (iii) support-free catalytically active particles.

Within the context of the present invention, the term catalyst here comprises transition metal, which serves as catalytically active species ("main metal"), or optionally a precursor thereof, also optionally present support and optionally present doping.

"Solid support" is to be understood here as meaning those materials which are solid under the reaction conditions of the process according to the invention and which are appropriate for the shaping of the heterogeneous catalyst.

"Present in particulate form" is to be understood as meaning that the support in question is in the form of particles whose average diameter is in the range from 0.1 μm to 2 mm, preferably 0.001 to 1 mm, particularly preferably in the range from 0.005 to 0.5 mm, in particular 0.01 to 0.25 mm.

"Present in nonparticulate form" is to be understood as meaning that the support has, in at least one dimension (width, height, depth), more than 2 mm, preferably at least 5 mm, where at least one further dimension, for example one or both further dimensions, can be less than 2 mm in size, for example in the range from 0.1 μm to 2 mm. In another variant, support present in nonparticulate form has three dimensions which have a dimension of more than 2 mm, preferably at least 5 mm. A suitable upper limit is, for example, 10 m, preferably 10 cm.

Examples of supports which are present in nonparticulate form are metal meshes, for example steel meshes or nickel meshes, also wires such as steel wires or nickel wires, also moldings, for example beads, Raschig rings, strands and tablets.

In one embodiment of the present invention, catalyst is used in the form of moldings, for example in the form of tablets or strands.

Examples of particularly suitable dimensions of molding are tablets with dimensions 6-3 mm, 3-3 mm, 2-2 mm, and strands with a diameter in the range from 1.5 to 3 mm.

Examples of supports which are present in particulate form are powders, which may be free-flowing or suspended.

Examples of materials from which supports which are present in particulate form may be made are $Al_2O_3$, $SiO_2$, alumosilicates, hydrotalcite, $TiO_2$, $ZrO_2$, activated carbon, in particular $Al_2O_3$, $ZrO_2$, and $TiO_2$.

Examples of support-free catalytically active particles (iii) are Raney metals, for example Raney copper, Raney nickel and Raney cobalt. Support-free catalytically active particles can be present for example as sponge or skeletal catalysts.

Besides support and transition metal, the catalyst can comprise one or more molding agents, for example graphite or stearic acid.

Examples of transition metals which are suitable as catalytically active species ("main metal") in metal-containing catalyst for the process according to the invention are transition metals of groups 4 to 12 of the Periodic Table of the Elements, and specifically preferably transition metals of the first periods of groups 4 to 12 of the Periodic Table of the Elements, i.e. from Ti to Zn, and also transition metals of groups 8 to 11 in all periods of the Periodic Table of the Elements. Particularly preferred transition metals are Co, Ni and Cu, and also Pd and Pt.

Transition metal in catalyst which is used for the process according to the invention can be doped, for example with one or more other transition metals such as Zr, Mo, Mn or Ti, or with Ca, with Sn, with Al or with Na. Doping is to be understood here as meaning amounts of doped transition metal or Na, Al or Ca, which are introduced in the range from 0.1 to 2 mol % of transition metal, or Na, Sn, Al or Ca, based on main metal. Within the context of the present invention, however, customary accompanying trace elements originating from the production of main metal are deemed as being excluded from a doping.

In one embodiment of the present invention, heterogeneous catalysts are selected from Raney metals and transition metal applied to a solid support. Preferred transition metal (main metal) is selected from Ni, Cu and Co.

To produce a catalyst that is suitable for the process according to the invention, and to store it, transition metal is generally used as precursor, namely as compound, for example as oxide, hydroxide or oxide hydroxide, or as alloy, and the catalyst is activated before carrying out the process according to the invention or in situ, preferably by means of reduction or by removing at least one component of the alloy in question. Preferably, transition metal in the heterogeneous catalyst is present while the process according to the invention is carried out proportionately at least at times in oxidation state zero.

In one embodiment of the present invention, catalysts are selected from those materials in particulate form whose mass—in each case determined prior to activation with hydrogen—comprises:
in total in the range from 15 to 80% by weight of oxygen-containing compound(s) of aluminum, calculated as $Al_2O_3$, preferably 30 to 70% by weight, particularly preferably 35 to 65% by weight,
in total in the range from 5 to 35% by weight of oxygen-containing compound(s) of nickel, calculated as NiO, preferably in the range from 10 to 30% by weight, particularly preferably in the range from 12 to 28% by weight, very particularly preferably 15 to 25% by weight,
in total in the range from 5 to 35% by weight of oxygen-containing compound(s) of cobalt, calculated as CoO, preferably in the range from 10 to 30% by weight, particularly preferably in the range from 12 to 28% by weight, very particularly preferably 15 to 25% by weight, in total in the range from 1 to 20% by weight of oxygen-containing compound(s) of copper, calculated as CuO, preferably 2 to 18% by weight, particularly preferably 5 to 15% by weight, in total in the range from 0.2 to 5% by weight of oxygen-containing compound(s) of tin, calculated as SnO, preferably in the range from 0.4 to 4.0% by weight, particularly preferably in the range from 0.6 to 3.0% by weight, very particularly preferably in the range from 0.7 to 2.5% by weight.

In one embodiment of the present invention, catalysts are selected from those materials in particulate form whose mass—in each case determined prior to activation with hydrogen—comprises:

22 to 45% by weight, preferably 25 to 40% by weight, of oxygen-containing compounds of zirconium, calculated as $ZrO_2$, 1 to 30% by weight, preferably 2 to 25% by weight, particularly preferably 5 to 15% by weight, of oxygen-containing compounds of copper, calculated as CuO, 5 to 50% by weight, preferably 15 to 45% by weight, particularly preferably 25 to 40% by weight, of oxygen-containing compounds of nickel, calculated as NiO, 5 to 50% by weight of oxygen-containing compounds of cobalt, calculated as CoO, 0 to 10% by weight of oxygen-containing compounds of aluminum and/or manganese, where the weight ratio of zirconium, calculated as $ZrO_2$, to aluminum and/or manganese, calculated as $Al_2O_3$ and/or $MnO_2$, is preferably at least 2.5, very particularly preferably 0% by weight of oxygen-containing compounds of aluminum and/or manganese, 0 to 5% by weight, preferably 0% by weight, of oxygen-containing compounds of molybdenum, calculated as $MoO_3$.

In one embodiment of the present invention, catalysts are selected from those materials in particulate form whose mass—in each case determined prior to activation with hydrogen—comprises:

50 to 95% by weight, preferably 55 to 85% by weight, particularly preferably 60 to 80% by weight, of oxygen-containing compounds of zirconium, calculated as $ZrO_2$, 5 to 50% by weight, preferably 15 to 45% by weight, particularly preferably 20 to 40% by weight, of oxygen-containing compounds of nickel, calculated as NiO.

In one embodiment of the present invention, the molar ratio of nickel to copper is greater than 1, particularly preferably greater than 1.2, very particularly preferably in the range from 1.8 to 8.5.

Preferably, the catalytically active mass of catalysts used in the process according to the invention comprises no rhenium, no ruthenium, no iron and/or no zinc, in each case neither in metallic (oxidation state=0) nor in ionic (oxidation state≠0).

In one embodiment of the present invention, catalyst suitable for process according to the invention has a BET surface area in the range from 1 to 1000 m$^2$/g, preferably from 10 to 500 m$^2$/g, measured by $N_2$ adsorption in accordance with DIN 66131.

Different processes are possible for producing preferred catalysts of variant (i) and (ii) used in the process according to the invention. Suitable catalysts of variant (i) and (ii) are obtainable, for example, by kneading pulverulent mixtures of the hydroxides, carbonates, oxides and/or other salts of the components with water and subsequent extrusion and tempering (heat treatment) of the resulting mass.

Preferably, precipitation methods are used for producing the catalysts of variant (i) and (ii) used in the process according to the invention. Thus, preferred catalysts can be obtained for example by means of a joint precipitation of nickel, cobalt, copper and tin components from an aqueous salt solution comprising these elements by means of bases in the presence of a slurry of a sparingly soluble, oxygen-containing aluminum, titanium, silicon and/or zirconium compound (precipitate) and subsequent washing, drying and calcining of the resulting precipitate. Sparingly soluble, oxygen-containing aluminum, titanium, silicon and/or zirconium compounds which can be used are, for example, their oxides, oxide hydrates, phosphates, borates and silicates. Slurries of the sparingly soluble oxygen-containing aluminum, titanium, silicon and/or zirconium compounds can be prepared by suspending finely particulate powders of such compounds in water with vigorous stirring. Preferably, slurries of sparingly soluble oxygen-containing aluminum, titanium, silicon or zirconium compounds are prepared by precipitating the corresponding sparingly-soluble oxygen-containing aluminum, titanium, silicon and zirconium compounds from aqueous solutions of aluminum, titanium, silicon and zirconium compounds by means of base.

Preferably, catalysts of variant (i) and (ii) used in the process according to the invention are prepared via a joint precipitation (mixed precipitation) of all of their components. For this purpose, an aqueous salt solution comprising the catalyst components is expediently admixed, at elevated temperature and with stirring, with an aqueous base—for example sodium carbonate, sodium hydroxide, potassium carbonate or potassium hydroxide—until the precipitation is complete. It is also possible to work with alkali-metal-free bases such as ammonia, ammonium carbonate, ammonium hydrogen carbonate, ammonium carbamate, ammonium oxalate, ammonium malonate, urotropin, urea, etc. The type of salts used is generally not critical: since in this procedure what matters is primarily the solubility in water of the salts, one criterion is their good solubility in water required for producing these relatively highly concentrated salt solutions. It is considered to be self explanatory that when selecting the salts of the individual components, naturally only salts are selected with those anions which do not lead to disturbances, whether by causing undesired precipitations or by hindering or preventing precipitation as a result of complexation.

The precipitates obtained during these precipitation reactions are generally chemically nonuniform and consist inter alia of mixtures of the oxides, oxide hydrates, hydroxides, carbonates and insoluble and basic salts of the metals used. For the filterability of the precipitates, it may prove favorable if they are aged, i.e. if they are left as they are for some time after the precipitation, optionally at elevated temperature and while passing air through.

The precipitates obtained after precipitation processes can be further processed to give catalysts of variant (i) and (ii) used in the process according to the invention by methods known per se. Initially, the precipitates are washed. The content of alkali metal which has been introduced via the (mineral) base possibly used as precipitating agent can be influenced by the duration of the washing and by the temperature and amount of the wash water. In general, the content of alkali metal will decrease as the washing time increases or the temperature of the wash water increases. After the washing, the precipitates can be dried, generally at 80 to 200° C., preferably at 100 to 150° C., and then calcined. The calcining can be carried out at temperatures between 300 and 800° C., preferably at 400 to 600° C., in particular at 420 to 550° C.

In another embodiment, catalysts of variant (i) and (ii) used in the process according to the invention can also be produced by impregnating aluminum oxide (Al$_2$O$_3$), titanium dioxide (TiO$_2$), silicon dioxide (SiO$_2$) or zirconium dioxide (ZrO$_2$), which is present in each case for example in the form of powders or moldings, such as strands, tablets, beads or rings, or mixtures of at least two of the aforementioned oxides with transition metal salt solution.

Aluminum oxide is used for example in the amorphous, gamma, theta and/or delta form, as aluminum oxohydroxide (boehmite), preferably in the gamma form.

Zirconium dioxide can be used for example in amorphous, monoclinic, tetragonal or cubic modification, preference being given to the monoclinic, tetragonal and cubic modification. Particular preference is given to the monoclinic modification.

Moldings can be produced by methods known per se.

In one embodiment of the present invention, 0.1 to 120% by weight of catalyst is used, based on α-ketocarboxylic acid of the general formula (II).

The process according to the invention is carried out at a temperature in the range from 50 to 200° C., preferably 75 to 175° C. and particularly preferably from 100 to 150° C.

In one embodiment of the process according to the invention, it is carried out at a pressure in the range from atmospheric pressure to 300 bar, preferably 20 to 250 bar, particularly preferably from 100 to 200 bar.

The process according to the invention can be carried out batchwise, continuously or semicontinuously.

In one embodiment of the present invention, the entire reaction mixture or certain components of the reaction mixture can be circulated, for example nitrogen compound, in particular ammonia, or aqueous solution of α-ketocarboxylic acid of the general formula (II).

In one embodiment of the present invention, the process according to the invention can be carried out batchwise at an essentially constant temperature, for example at a temperature which fluctuates by 10° C. or less during the process according to the invention, preferably by 5° C. or less.

In one embodiment of the present invention, the process according to the invention is carried out over a duration in the range from 1 minute to 48 hours. If it is desired to carry out the process according to the invention continuously, then duration should be understood as meaning the average residence time.

In one embodiment of the present invention, the process according to the invention is carried out as suspension of at least one catalyst according to variant (i) or (iii), and specifically with a reaction time in the range from 1 to 48 hours, preferably 2 to 24 hours.

In another embodiment of the present invention, the process according to the invention is carried out with a catalyst according to variant (ii), and specifically with a reaction time in the range from 1 minute to 10 hours, preferably 30 minutes to 5 hours.

When calculating the time, periods of time which are used for activities such as heating, cooling, working up the reaction mixture, isolating racemic α-amino acid, decompressing or activating the catalyst should not be taken into consideration.

In one embodiment of the present invention, mixing can be used to carry out the process according to the invention, for example by means of stirring, shaking, rolling, circulating, pumping by static mixers or pneumatic mixing.

Without intending to give preference to a specific theory, it is assumed that in the course of the process according to the invention α-ketocarboxylic acid is converted to the corresponding α-iminocarboxylic acid and is then reduced to racemic α-aminocarboxylic acid.

This gives a reaction mixture which comprises water and alkali metal salt of racemic α-amino acid and can have further constituents, for example catalyst (residues), starting material such as α-ketocarboxylic acid or nitrogen compound, in particular ammonia, or furthermore decomposition products of α-ketocarboxylic acid, for example propionic acid, acetic acid or formic acid. Preferably, however, the reaction mixture comprises only extremely small fractions of decomposition product(s) of α-ketocarboxylic acid.

In one embodiment of the present invention, the resulting reaction mixture is worked up. In a specific embodiment of the present invention, racemic α-amino acid or a salt of racemic α-amino acid is isolated.

For the work-up, one or more of the following activities, for example, can be carried out:
(i) deactivate catalyst,
(ii) separate off catalyst, which may be active or deactivated, for example by filtration, for example cake filtration or crossflow filtration, or by sedimentation or centrifugation,
(iii) completely or partially remove water and nitrogen compound, in particular ammonia, for example by evaporation, distillation or spray-drying,
(iv) neutralize nitrogen compound or in particular ammonia with acid, in particular with Brönsted acid, for example with sulfuric acid or hydrochloric acid,
(v) separate off by-products which can be formed for example as a result of reduction of α-ketocarboxylic acid used,
(vi) adjust pH, for example with Brönsted acid or Brönsted base,
(vii) separate off α-amino acid from unreacted α-ketocarboxylic acid by means of ion exchanger.

In one embodiment of the present invention, racemic α-amino acid or salt of racemic α-amino acid that is produced is recrystallized for the purposes of purification. Various solvents can be used for the recrystallization. Of suitability are, for example, water and water-containing mixtures, for example mixtures of water with ethanol. Preferably, recrystallization is from water or aqueous bases which have a pH in the range from 7.1 to 14, preferably 9 to 12. Suitable aqueous bases are dilute potassium hydroxide solution and in particular dilute sodium hydroxide solution.

Recrystallization can be carried out one or more times. Crystallized racemic α-amino acid or crystallized alkali metal salt of racemic α-amino acid can be separated off from the mother liquor, for example by decantation or filtration or combination of filtration and decantation.

In one embodiment, pure racemic α-amino acid or pure salt of racemic α-amino acid, for example pure sodium salt or pure potassium salt, or partially neutralized pure racemic α-amino acid is obtained.

Proof that the racemic α-amino acid (a) is the racemate is accomplished for example by polarimetry.

Alkali metal salts prepared by the process according to the invention of racemic α-amino acids of the general formula (I)

$$R^1\text{—CH(NH}_2\text{)—COOH} \qquad (I)$$

in which R$^1$ is selected from hydrogen, CH$_3$, C$_2$H$_5$, CH(CH$_3$)$_2$, (CH$_2$)$_2$COOH and CH$_2$OH, can be used especially for making for example complexing agents, for example nitrilotriacetic acid (where R$^1$=hydrogen), methylglycinediacetic acid (where R$^1$=CH$_3$), or glutaminic acid diacetic acid (where R$^1$=(CH$_2$)$_2$COOH).

The invention is illustrated by the following working examples.

I. PREPARATION OF THE SODIUM SALT OF RACEMIC ALANINE 50 g of a 60% by weight aqueous solution of the sodium salt of pyruvic acid (corresponding to 0.27 mol of sodium pyruvate) was charged to an autoclave together with 5 g of a Raney Ni catalyst. The autoclave was closed, and $NH_3$ (66 g; 3.88 mol) was injected cold. The pressure was increased to 20 bar with hydrogen. The autoclave was then heated to 100° C. The pressure was increased to 100 bar with hydrogen, and the reaction mixture was stirred over a period of 3 hours under this condition. The autoclave was then cooled to room temperature and decompressed. The catalyst was filtered off from the reaction mixture and the filtrate was analyzed by NMR spectroscopy. It comprised, as main product, the sodium salt of the racemic alanine. This was able to be isolated easily.

II. COMPARATIVE EXAMPLE

Attempt to Prepare Racemic Alanine from Pyruvic Acid

Example I was repeated, but using 50 g of a 60% by weight aqueous solution of pyruvic acid. This gave a product mixture which comprised numerous decomposition products and could neither be separated nor purified by simple recrystallization.

The invention claimed is:

1. A process for preparing an alkali metal salt of a racemic α-amino acid of formula (I):

$R^1$—CH($NH_2$)—COOH     (I), the process comprising reacting at least one nitrogen compound with an alkali metal salt of a corresponding α-ketocarboxylic acid or glyoxalic acid in the presence of at least one heterogeneous catalyst and hydrogen at a temperature ranging from 50 to 200° C., to form the alkali metal salt of the racemic α-amino acid of formula (I), wherein:
- $R^1$ is a group selected from the group consisting of hydrogen, $CH_3$, $C_2H_5$, $CH(CH_3)$, $(CH_2)_2COOH$ and $CH_2OH$;
- the heterogeneous catalyst comprises at least one transition metal; and
- the nitrogen compound is selected from the group consisting of a primary amine, a secondary amine and ammonia.

2. The process of claim 1, wherein the at least one heterogeneous catalyst is selected from the group consisting of a Raney metal and a transition metal applied to a solid support.

3. The process of claim 1, wherein the transition metal is selected from the group consisting of Pd, Pt, Ni, Cu and Co.

4. The process of claim 1, wherein the transition metal in the heterogeneous catalyst is present during the process at least at times in oxidation state zero.

5. The process of claim 1, wherein the nitrogen compound is ammonia.

6. The process of claim 1, comprising reacting the at least one nitrogen compound with an alkali metal salt of pyruvic acid.

7. The process of claim 1, comprising reacting the at least one nitrogen compound with sodium pyruvate.

8. The process of claim 1, wherein the process is carried out at a pressure in the range from atmospheric pressure to 300 bar.

9. The process of claim 1, wherein the process is carried out in aqueous medium.

10. The process of claim 1, further comprising purifying the alkali metal salt of the racemic α-amino acid by recrystallization.

* * * * *